United States Patent [19]
Santilli et al.

[11] Patent Number: 6,099,468
[45] Date of Patent: Aug. 8, 2000

[54] RETRACTOR FOR PARTIAL STERNOTOMY

[75] Inventors: Albert N. Santilli, Pepper Pike, Ohio; Amit Patel, Dallas, Tex.

[73] Assignee: Kapp Surgical Instrument, Inc., Cleveland, Ohio

[21] Appl. No.: 09/232,496

[22] Filed: Jan. 15, 1999

[51] Int. Cl.[7] .................................................. A61B 17/02
[52] U.S. Cl. ........................................................ 600/232
[58] Field of Search ................................. 600/201, 205, 600/227, 231, 232, 233, 234

[56] References Cited

U.S. PATENT DOCUMENTS

| | | |
|---|---|---|
| Re. 34,150 | 12/1992 | Santilli et al. . |
| 2,812,759 | 11/1957 | Taylor . |
| 3,168,093 | 2/1965 | Gauthier . |
| 3,221,743 | 12/1965 | Thompson et al. . |
| 4,492,229 | 1/1985 | Grunwald ............................. 600/232 X |
| 4,627,421 | 12/1986 | Symbas et al. .......................... 600/232 |
| 4,726,356 | 2/1988 | Santilli et al. .......................... 600/232 |
| 4,865,019 | 9/1989 | Phillips . |
| 5,167,223 | 12/1992 | Koros et al. ............................. 600/232 |
| 5,755,660 | 5/1998 | Tyagi .................................. 600/232 X |

OTHER PUBLICATIONS

St. Jude Medical, Inc. Flyer on Cosgrove Mitral Valve Retractor Copyright 1993.

*Primary Examiner*—Jeffrey A. Smith
*Attorney, Agent, or Firm*—Rankin, Hill, Porter & Clark LLP

[57] ABSTRACT

A retractor for use in partial sternotomy includes a toothed crossbar to which a pair of small, parallel grips are attached. The first grip is attached to an arm which is fixed to one end of the crossbar. The second grip is attached to an arm which is movably attached to the crossbar by a pinion, thereby permitting the second grip to be moved along the crossbar toward or away from the first grip. A first rod is connected to the fixed arm by means of a bracket, while a second rod is connected to the movable arm by means of a similar bracket. Retractor blades of different configurations can be connected to the rods by universal clamps. Suture holders are disposed atop each of the arms. A holder for a carbon dioxide tube can be removably connected to the toothed portion of the crossbar.

13 Claims, 3 Drawing Sheets

RETRACTOR FOR PARTIAL STERNOTOMY

BACKGROUND OF THE INVENTION

1. Field of the Invention

The invention relates to retractors that are used in cardiovascular surgery and, more particularly, to a retractor that permits such operations to be conducted with reduced trauma to the patient.

2. Description of the Prior Art

In the course of such operative procedures as mitral valve surgery and mammary artery surgery, it is necessary to expose the heart. Such exposure traditionally has been accomplished by cutting an incision completely through the sternum and retracting the sternum. This procedure is known as a full sternotomy.

The retraction is accomplished by a retractor that employs parallel grips that engage the edges of the separated sternum. The grips are mounted on a toothed crossbar. One of the grips is fixed to one end of the crossbar, while the other grip is movably mounted to the crossbar by means of a pinion that engages the teeth of the crossbar. Upon rotating the pinion, the movable grip can be moved away from the fixed grip, thereby retracting the sternum so as to expose the heart. A retractor of the type described is shown in U.S. Re. 34,150, issued Dec. 29, 1992 to A. E. Santilli and D. M. Cosgrove III ("the '150 patent"), the disclosure of which is incorporated herein by reference.

After the sternum has been retracted, it is necessary to retract portions of the heart in order to expose diseased or defective parts thereof. Such retraction has been accomplished by attaching a cardiovascular retractor to one of the grips of the sternum retractor. The cardiovascular retractor, in preferred form, includes a horizontal rod to which retractor blades having elongate handles are attached by means of universal clamps. The rod is spaced above the grip a considerable distance in order to permit the blades to have access to the heart at a favorable angle. The blades can be moved so as to engage portions of the heart to be retracted. Thereafter, upon pulling the blades and locking them in place by tightening the universal clamps, the heart can be retracted in any manner desired and maintained in that position as long as necessary.

The blades in the described construction can be moved back and forth, up and down, side to side, and they can be pivoted about the longitudinal axis of the handle. Such versatility enables the device to be used for virtually any type of heart operation where retraction is required. A preferred example of the device in question is disclosed in the '150 patent.

While the retractor disclosed in the '150 patent is effective for retraction of the sternum and subsequent retraction of the heart, unfortunately the operative technique is very invasive. That is, the complete splitting of the sternum that occurs during a full sternotomy, coupled with retraction of the sternum, is an extremely traumatic procedure. The recovery time from such a procedure can be significant. Further, the patient will experience considerable pain and discomfort during the recovery process. It is possible that the trauma associated with the process can have a negative impact on the patient's recovery from the operation.

Desirably, a retractor would exist that would permit surgical procedures to be performed that are less invasive than are possible with presently available retractors. Preferably, any such less invasive retractor would be relatively small and lightweight compared with prior retractors.

SUMMARY OF THE INVENTION

In accordance with the present invention, a new and improved retractor is disclosed that is less invasive than prior retractors. By using the present invention, a full sternotomy does not have to be performed in order to conduct heart operations. That is, a partial sternotomy can be performed using the reteractor of the present invention. The retractor also can be used for minimally invasive off-cardio pulmonary by-pass coronary revascularization.

The retractor according to the invention includes a pair of very small parallel grips that are mounted to a toothed crossbar. The grips are disposed at the ends of arms that extend at right angles from the crossbar. One of the arms is fixed to one end of the crossbar, while the other arm is movable along the crossbar by means of a pinion so that the grips can be moved toward or away from each other.

A first rod is connected to the fixed arm by means of a first bracket. A second rod is connected to the movable arm by means of a second bracket. The first rod is L-shaped, while the second rod is straight. The brackets are slidable along the arms in order to permit the longitudinal position of the rods relative to the arms to be adjusted. The brackets are large enough that the rods are disposed above the arms a desired distance.

The rods enable one or more small retractor blades of conventional design having elongate handles to be used to retract portions of the heart. Each retractor blade is connected to one of the rods by means of a universal clamp that grasps both the handle of the blade and the rod. Each clamp includes a nut that enables the clamp to be tightened or loosened with one hand. The clamps permit the blades to be moved to any position that may be desired by the surgeon.

The invention includes suture holders that are connected to each of the arms. In the preferred embodiment, the suture holders are in the form of coil springs. The invention also includes a holder for a tube, such as a carbon dioxide tube, that can be placed in the operative site. The holder is in the form of a clip that frictionally engages the toothed crossbar and a sleeve through which the tube is fitted.

As will be appreciated from the foregoing description, the retractor according to the invention is less invasive than prior retractors. By using the retractor according to the invention, a partial sternotomy, rather than a full sternotomy, can be performed in order to have access to the heart. The foregoing features and advantages will be apparent from the accompanying drawings and the description that follows.

DESCRIPTION OF THE PREFERRED EMBODIMENT

Figure 1:
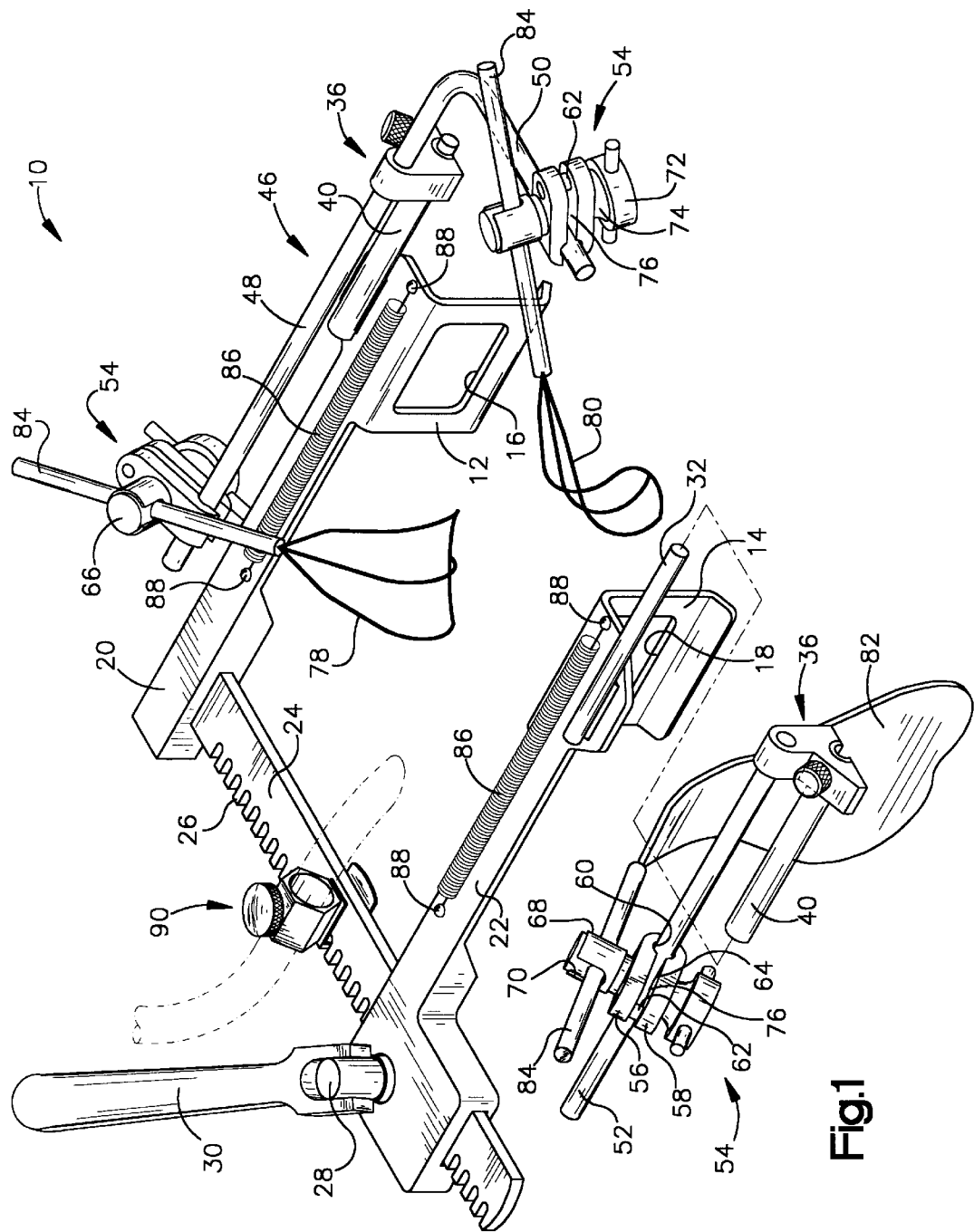
FIG. 1 is a perspective view of a retractor according to the invention.
Figure 2:
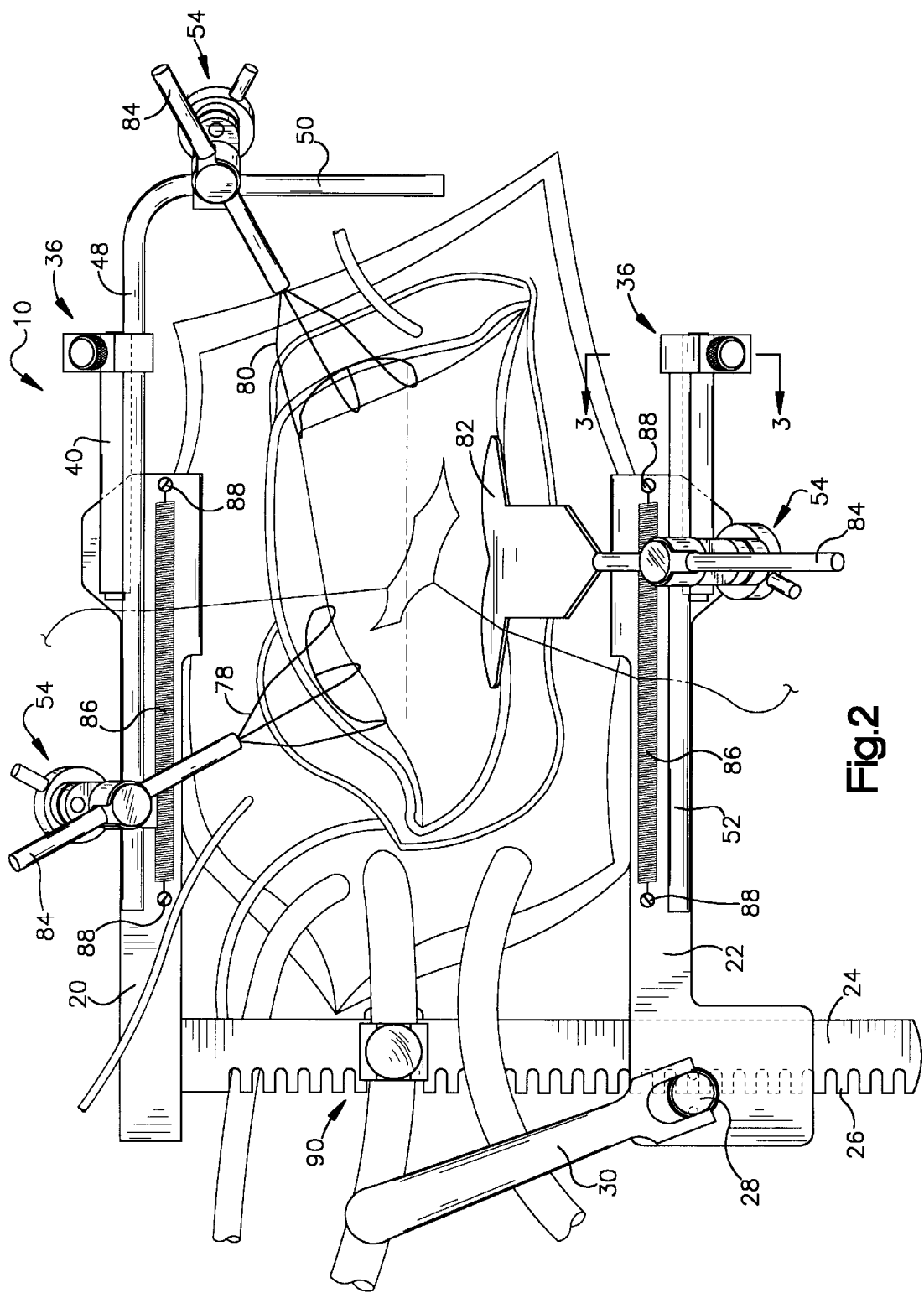
FIG. 2 is a view similar to FIG. 1 showing the retractor being used during surgery.

Referring particularly to FIGS. 1 and 2, a retractor according to the invention is indicated by the reference numeral 10. The retractor 10 is of the Finochietto type. The retractor 10 includes a pair of small, generally rectangular parallel grips 12, 14. The grips 12, 14 have rectangular openings 16, 18 formed therein, respectively. The grips 12, 14 are mounted at the ends of arms 20, 22, respectively.

The arms 20, 22 extend at right angles away from a crossbar 24 having a plurality of spaced teeth 26. The arm 20 is fixed to the crossbar 24, while the arm 22 is movable along the crossbar 24 so as to move the grip 14 toward or away from the grip 12. Movement of the arm 22 is accomplished by a pinion 28 that engages the teeth 26 of the crossbar 24. A handle 30 is connected to the pinion 28 for purposes of rotating the pinion 28.

A cylindrical bar 32 is mounted atop each of the arms 20, 22. The bar 32 is secured to the arms 20, 22 by means of welds 34. As can be seen in FIGS. 1 and 2, the bars 32 are disposed at the end of the arms 20, 22. The longitudinal axis of the bars 32 is parallel with that of the arms 20, 22.

Figure 3:
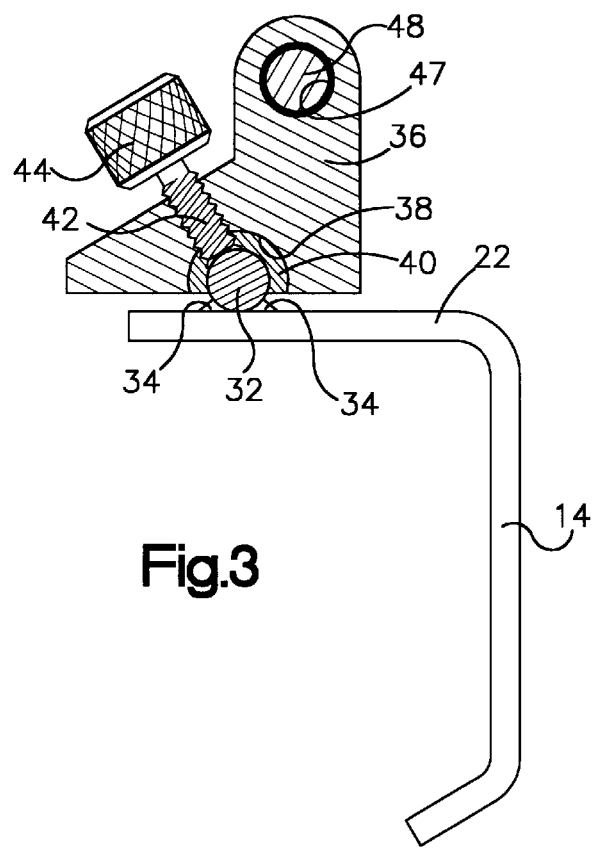
FIG. 3 is a cross-sectional view of a rod-supporting bracket according to the invention.

A vertically extending bracket 36 is secured to each of the bars 32. Because the brackets 36 are mirror images of each other, only one of them will be described herein. Referring particularly to FIG. 3, the bracket 36 has a longitudinally extending groove 38 within which a sleeve 40 is disposed. The sleeve 40 is open on its underside. The inner diameter of the sleeve 40 is slightly larger than the outer diameter of the bar 32 so that a relatively tight fit between the two can be made.

The bracket 36 includes a threaded pin 42 that has a knob 44. The pin 42 extends through openings in the bracket 36 and the sleeve 40. The bracket 36 can be moved along the bar 32 until a desired longitudinal position has been attained. Thereafter, the end of the pin 42 can be tightened against the bar 32 so as to secure the bracket 36 in place.

A cylindrical first rod 46 extends through an opening 47 formed in the bracket 36 that is connected to the fixed arm 20. The rod 46 is secured within the opening 47 by means of silver solder or any other suitable securement technique. The rod 46 is L-shaped, with a first section 48 that is disposed parallel to the longitudinal axis of the arm 20 and a second section 50 that is disposed perpendicular to the first section 48. The second section 50 extends toward the second arm 22. A second rod 52 is connected to the other bracket 36. The second rod 52 is similar to the rod 46 but includes only a portion that is parallel to the longitudinal axis of the movable arm 22. As with the rod 46, the rod 52 is secured within the opening 47 by silver solder or other suitable technique.

The retractor 10 includes several universal clamps 54 that are used to hold retractor blades in a variety of desired positions. Because the clamps 54 are identical, only one of them will be described herein. The clamp 54 includes an upper finger 56 and a lower finger 58. The fingers 56, 58 are disposed immediately adjacent each other. A groove 60 is formed in the ends of each of the fingers 56, 58 so that the grooves 60 face each other. A guide pin 62 extends between, and connects, the fingers 56, 58. Similarly, a threaded pin 64 extends through the fingers 56, 58. The pin 64 has a head 66 that contains a transverse bore. A sleeve 68 is disposed about the head 66. The sleeve 68 includes a pair of opposed, U-shaped slots 70. A nut 74 is threaded onto the pin 64, which nut 72 includes a tapered side 72 that engages the underside of the lower finger 58. A spring 76 is disposed between the opposed fingers 56, 58. The spring 76 is disposed about that portion of the threaded pin 64 that extends between the fingers 56, 58.

A plurality of retractor blades 78, 80, 82 are provided for use with the invention. Each of the blades 78, 80, 82 includes an elongate, cylindrical handle 84. The handle 84 is of a size that can be fitted through the bore in the head 66 and the slots 70 (when the slots 70 are aligned with the bore). The retractor blade 78, 80, 82 are of conventional design, although they are made relatively small to permit partial sternotomies to be conducted.

As will be apparent from an examination of FIGS. 1 and 2, the handles 84 can be fitted through the aligned bores 67 and slots 70 and moved to any position desired. When it is desired to fix a selected retractor blade 78, 80, 82 in any desired position, the nut 72 is tightened. As the head 66 is pulled toward the nut 72, the handle 84 will be compressed against the lower edges of the slots 70, thereby tightening the handle 84 in place. Continued tightening of the nut 72 will cause the fingers 56, 58 to be moved toward each other against the opposing force of the spring 76. Eventually, the grooves 60 will tightly engage a selected rod 46, 52, thereby locking the clamp in place on the rod 46, 52. By virtue of the foregoing construction, the user can use one hand to grasp the handle 84 and retract the selected retractor blade 78, 80, 82 to any desired position. Using the other hand, the nut 72 can be tightened after the desired position of the blade 78, 80, 82 has been attained. This is a very convenient and effective way to securely position the blades 78, 80, 82 in a desired position.

The retractor 10 includes a suture holder 86 that is disposed atop each of the arms 20, 22. As shown in FIGS. 1 and 2, the suture holders 86 are in the form of springs. The ends of the springs 86 are secured to the upper surface of the arms 20, 22 by means of screws 88. The spaces between adjacent coils can receive sutures, thereby enhancing the convenience of the retractor 10 for the surgeon.

Figure 4:
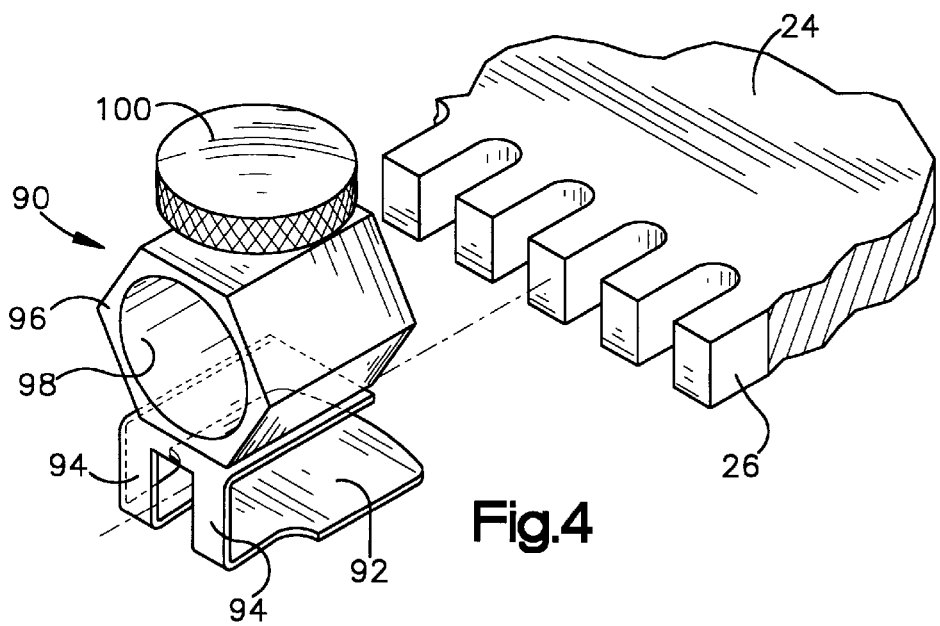
FIG. 4 is a perspective view of a tube holder according to the invention.

The retractor 10 also includes a tube holder 90 for securing tubes such as carbon dioxide tubes in a desired position. Referring particularly to FIG. 4, the tube holder 90 includes a clip 92 having spaced legs 94. The legs 94 are of a size and shape to fit between adjacent teeth 26 included as part of the crossbar 24. The tube holder 90 includes a sleeve 96 having a bore 98. A set screw 100 is carried by the sleeve 96 and opens into the bore 98. Accordingly, when a tube has been inserted through the bore 98, the set screw 100 can be used to tighten the tube within the bore 98 so as to prevent movement of the tube. If the tube needs to be repositioned, either the set screw 100 can be loosened and retightened, or the clip 92 can be repositioned laterally along the crossbar 24.

It is expected that the retractor 10 will be used as follows. Initially, the handle 30 will be rotated so that the arm 22 will be moved toward the arm 20. Accordingly, the grips 12, 14 will be immediately adjacent each other. Due to the small size and shape of the grips 12, 14, the thoracic cavity need be opened only a small amount, for example, a distance of about 4 inches. After inserting the grips 12, 14 into the incision, the sternum can be retracted by turning the handle 30 to move the grip 14 away from the grip 12.

After the grips 12, 14 have been moved apart, the brackets 36 are attached to the bars 32 as indicated in FIGS. 1 and 2. The knob 42 is tightened against the bar 32 to retain the bracket 36 and, hence, the rod 46, 52 in any desired longitudinal position. After the rods 46, 52 have been positioned as desired, the clamps 54 are used to position the retractor blades 78, 80, 82 as may be necessary to adequately expose the heart. During the course of surgery, the suture holders 86 can be used to conveniently hold sutures and prevent them from being lost or tangled. Also, one or more tube holders 90 can be used to quickly and conveniently secure tubes, such as carbon dioxide tubes, in any desired position.

Although the invention has been shown and described with respect to a certain preferred embodiment, various alterations and modifications may occur to others skilled in the art upon reading and understanding this specification. The patent is intended to include all such alterations and modifications and is limited only by the scope of the following claims.

What is claimed is:

1. A surgical retractor in which first and second arms having first and second grips, respectively, are connected to each other by a toothed crossbar, the first arm being rigidly connected to the crossbar at one end thereof and the second arm being movable along the crossbar toward or away from the first arm, comprising:

a first rod connected to the first arm for supporting one or more retractor blades, the first rod being generally L-shaped with first and second sections, the first section being disposed above the upper surface of the first arm and generally parallel to the first arm, the second section extending toward the second arm and generally perpendicular to the first section;

a second rod connected to the second arm for supporting one or more retractor blades, the second rod being disposed above the upper surface of the second arm and generally parallel to the first arm;

a first suture holder connected to the first arm; the first suture holder being disposed between the first section and the first arm; and a second suture holder connected to the second arm, the second suture holder being disposed between the second rod and the second arm.

2. The retractor of claim 1, wherein the first and second suture holders are in the form of coil springs.

3. The retractor of claim 2, wherein the springs have opposed ends, and the opposed ends are secured to the first and second arms by screws that connect the ends of the springs to the arms.

4. The retractor of claim 1, further comprising a holder for holding a gas-delivery tube, the holder being removably attached to the toothed crossbar.

5. The retractor of claim 4, wherein the holder comprises a clip having a pair of spaced legs that extend into the spaces on either side of a given tooth of the crossbar and a tube-grasping member attached to the clip.

6. The retractor of claim 5, wherein the tube-grasping member is in the form a sleeve through which the tube may extend.

7. The retractor of claim 6, further comprising a set screw included as part of the sleeve, the set screw being selectively engagable with the tube in order to compress the tube within the sleeve.

8. The retractor of claim 1, wherein the first and second rods each are secured to the arm by a vertically extending bracket that includes a longitudinally extending open-sided sleeve, the sleeve being of a size and shape to be fitted over a bar that is secured to the arm.

9. The retractor of claim 8, wherein the retractor blades have elongate handles and each retractor blade is connected to a selected rod by a universal clamp that engages both the rod and the handle of the retractor blade.

10. A surgical retractor in which first and second arms having first and second grips, respectively, are connected to each other by a toothed crossbar, the first arm being rigidly connected to the crossbar at one end thereof and the second arm being movable along the crossbar toward or away from the first arm, comprising:

a first rod connected to the first arm for supporting one or more retractor blades, the first rod being generally L-shaped with first and second sections, the first section being disposed above the upper surface of the first arm and generally parallel to the first arm, the second section extending toward the second arm and generally perpendicular to the first section;

a second rod connected to the second arm for supporting one or more retractor blades, the second rod being disposed above the upper surface of the second arm and generally parallel to the first arm;

first and second vertically extending brackets for securing the first and second rods to the first and second arms, respectively, each bracket including a longitudinally extending open-sided sleeve, the sleeve being of a size and shape to be fitted over a bar that is secured to each of the arms;

a first suture holder in the form of a coil spring connected to the first arm; the first suture holder being disposed between the first section and the first arm, the spring having opposed ends that are connected to the first arm by screws;

a second suture holder in the form of a coil spring connected to the second arm, the second suture holder being disposed between the second rod and the second arm, the spring having opposed ends that are connected to the second arm by screws; and a holder for holding a gas-delivery tube, the holder being removably attached to the toothed crossbar, the holder being in the form of a clip having a pair of spaced legs that extend into the spaces on either side of a given tooth of the crossbar and a tube-grasping member attached to the clip.

11. The retractor of claim 10, wherein the tube-grasping member is in the form a sleeve through which the tube may extend.

12. The retractor of claim 11, further comprising a set screw included as part of the sleeve, the set screw being selectively engagable with the tube in order to compress the tube within the sleeve.

13. The retractor of claim 10, further comprising retractor blades having elongate handles, each retractor blade being connected to a selected rod by a universal clamp that engages both the rod and the handle of the retractor blade.

* * * * *